United States Patent
Ferguson et al.

(10) Patent No.: US 7,365,839 B2
(45) Date of Patent: Apr. 29, 2008

(54) PROCESS AND COMPOSITIONS FOR SYNTHETIC CALIBRATION OF BIO-PHOTONIC SCANNERS

(75) Inventors: Scott Ferguson, Spanish Fork, UT (US); Stephen J. Poole, Provo, UT (US)

(73) Assignee: Nu Skin International, Inc., Provo, UT (US)

( * ) Notice: Subject to any disclaimer, the term of this patent is extended or adjusted under 35 U.S.C. 154(b) by 722 days.

(21) Appl. No.: 10/981,139

(22) Filed: Nov. 3, 2004

(65) Prior Publication Data

US 2006/0092411 A1    May 4, 2006

(51) Int. Cl.
G01J 1/10       (2006.01)
G01J 3/44       (2006.01)
(52) U.S. Cl. .................... 356/243.1; 356/301
(58) Field of Classification Search ............ 356/301, 356/243.1, 243.4, 243.5; 600/476, 477, 473, 600/406
See application file for complete search history.

(56) References Cited

U.S. PATENT DOCUMENTS

| | | | |
|---|---|---|---|
| 4,318,057 A | 3/1982 | Buchwald et al. |
| 4,500,995 A | 2/1985 | White |
| 4,758,081 A | 7/1988 | Barnes |
| 4,807,240 A | 2/1989 | Goldstone |
| 4,832,483 A | 5/1989 | Verma |
| 4,852,579 A | 8/1989 | Gilstad et al. |
| 4,858,238 A | 8/1989 | Cardimona |
| 5,034,228 A | 7/1991 | Meybeck et al. |
| 5,124,313 A | 6/1992 | Schaeffer et al. |
| 5,202,826 A | 4/1993 | McCarthy |
| 5,243,983 A | 9/1993 | Tarr et al. |
| 5,275,168 A | 1/1994 | Reintjes et al. |

(Continued)

FOREIGN PATENT DOCUMENTS

EP       0722692 A1       7/1996

(Continued)

OTHER PUBLICATIONS

Brody, J.E., "Health Factor in Vegetables Still Elusive," The New York Times, Section C, p. 1, Feb. 21, 1995.

(Continued)

*Primary Examiner*—F. L. Evans
*Assistant Examiner*—Abdullahi Nur
(74) *Attorney, Agent, or Firm*—Stuart Hemphill Dorsey & Whitney LLP

(57) ABSTRACT

A method, apparatus, and set of compositions are disclosed for calibrating a bio-photonic scanner. The scanner detects selected molecular structures of tissues, nondestructively, in vivo. The apparatus may include a computer, including processor and memory connecting to the scanner, including an illuminator to direct light nondestructively onto tissue in vivo, a detector to detect an intensity of a radiant response of the tissue to the light, and a probe to direct light onto the subject and receive a radiant response back into the detector. The apparatus is calibrated using a synthetic material to mimic the radiant response of live tissue, correcting for background fluorescence and elastic scattering. Dopants in a matrix of synthetic material mimic selected molecular structures of tissue. Matrix materials include a dilatant compound, and dopants include biological materials as well as K-type polarizing film powdered and mixed.

11 Claims, 11 Drawing Sheets

U.S. PATENT DOCUMENTS

| | | | |
|---|---|---|---|
| 5,290,605 | A | 3/1994 | Shapira |
| 5,303,026 | A | 4/1994 | Strobl et al. |
| 5,304,170 | A | 4/1994 | Green |
| 5,346,488 | A | 9/1994 | Prince et al. |
| 5,348,018 | A | 9/1994 | Alfano et al. |
| 5,418,797 | A | 5/1995 | Bashkansky et al. |
| 5,421,337 | A | 6/1995 | Richards-Kortum et al. |
| 5,432,610 | A | 7/1995 | King et al. |
| 5,451,785 | A | 9/1995 | Faris |
| 5,452,723 | A | 9/1995 | Wu et al. |
| 5,537,314 | A | 7/1996 | Kanter |
| 5,553,616 | A | 9/1996 | Ham et al. |
| 5,556,612 | A | 9/1996 | Anderson et al. |
| 5,567,628 | A | 10/1996 | Tarcha et al. |
| 5,579,773 | A | 12/1996 | Vo-Dinh et al. |
| 5,590,660 | A | 1/1997 | MacAulay et al. |
| 5,643,623 | A | 7/1997 | Schmitz et al. |
| 5,657,754 | A | 8/1997 | Rosencwaig |
| 5,666,223 | A | 9/1997 | Bennett et al. |
| 5,697,373 | A | 12/1997 | Richards-Kortum et al. |
| 5,733,507 | A | 3/1998 | Zakim |
| 5,734,838 | A | 3/1998 | Robinson et al. |
| 5,873,831 | A | 2/1999 | Bernstein et al. |
| 6,134,533 | A | 10/2000 | Shell |
| 6,205,354 | B1 | 3/2001 | Gellermann et al. |
| 6,408,281 | B1 | 6/2002 | Shell et al. |
| 6,415,265 | B1 | 7/2002 | Shell et al. |
| 6,421,648 | B1 | 7/2002 | Gagnon et al. |
| 6,690,966 | B1 | 2/2004 | Rava et al. |
| 7,039,452 | B2 | 5/2006 | McClane et al. |
| 2002/0133080 | A1* | 9/2002 | Apruzzese et al. ......... 600/477 |
| 2003/0030798 | A1* | 2/2003 | Samsoondar et al. .... 356/243.1 |
| 2003/0130579 | A1 | 7/2003 | McClane et al. |

FOREIGN PATENT DOCUMENTS

| | | |
|---|---|---|
| WO | WO 92/10131 | 6/1992 |
| WO | WO 92/15008 | 9/1992 |

OTHER PUBLICATIONS

Bone, R.A., Landrum, J.T., and Cains, A, "Optical Density Spectra of the Macular Pigment In Vivo and In Vitro," Vision Res., vol. 32, No. 1, pp. 105-110, 1992.

Handelman, G.J., Snodderly, D.M., Krinsky, N.L., Russett, M.D., and Adler, A.J., "Bilogical Control of Primate Macular Pigment," Inv. Ophthalmol. Vis. Sci., vol. 32, No. 2, pp. 257-267, Feb. 1991.

Hammond, B.R., Fuld, K., and Curran-Celentano, J., "Macular Pigment Density in Monozygotic Twins," Invest. Ophthalmoo. Vis. Sci., vol. 36, No. 12, pp. 2531-2541, Nov. 1995.

Seddon, J.M., Ajani, U.A., Sperduto, R.D., Hiller, R., Blair, N., Burton, T.C., Farber, M.D., Gragoudas, E.S., Haller, Jr., Miller, D.T., Yannuzzi, L.A., and Willet, W., "Dietary Carotenoids, Vitamins A, C and E, and Advanced Age-Related Macular Degneration," J. Am. Med. Assoc., vol. 272, No. 18, pp. 1413-1420, Nov. 9, 1994.

Schalch, Wolfgang, "Carotenoids in the Retina—A Review of Their Possible Role in Preventing or Limiting Damage Caused by Light and Oxygen," Free Radicals and Aging, Basel, Switzerland: Birkhauser Verlag, pp. 280-298, 1992.

Tom C. Bakker Schut; Gerwin J. Puppels; Yvonne M. Kraan; Jan Greve; Louis L.J. Van Der Maas; and, Carl G. Figdor, "Intracellular Carotenoid Levels Measured by Raman Microspectroscopy: Comparison of Lymphocytes from Lung Cancer Patients and Healthy Individuals," Int. J. Cancer (Pred. Oncol): 74, 20-25 (1997).

Monika Gniadecka; Hans C. Wulf; Ole F. Nielsen; Daniel H. Christensen; and, Jana Hercogova, "Distinctive Molecular Adnormalities in Benign and Malignant Skin Lesions: Studies by Raman Spectroscopy," Photochemistry and Photobiology, 1997, 66(4): 418-423.

Berendshot, Tos T. J. M., et al., "Influence of Lutein Supplementation on Macular Pigment, Assessed with Two Objective Techniques," IOVS, Oct. 2000, vol. 41, No. 11, pp. 3322-3326.

Elsner, Ann E., et al, "Foveal Cone Photopigment Distribution: Small Alterations Associated witih Macular Pigment Distribution," IOVS, Nov. 1998, vol. 39, No. 12, pp. 2394-2404.

Edwin H. Land, *Some Aspects of the Development of Sheet Polarizers*, Journal of the Optical Society of America, Dec. 1951, vol. 41, No. 12, pp. 957-963.

D. Gill et al., *Resonance Raman Spectra of Conjated Polyvinylenes in Dichroic Polarizing Sheets (Polaroid KN-42)*, Chemical Physics Letters, Mar. 15, 1971, vol. 8, No. 6, pp. 634-636.

Pharmanex Biophotonic Scanner Operating Manual, pp. 1-38, no date on it.

Material Safety Data Sheet, Dow Corning (R) 3179 Dilatant Compound, Jul. 7, 1997, pp. 1-6.

Linear and Circular Polarizers, Vikniti Display Enhancement, 3M Corporation, 2001 pp. 1-8.

S.E.J. Bell, E.S.O. Bourguignon, A. O'Grady, J. Villaumie, and A.C. Dennis, *Extracting Raman spectra from highly flourescent samples with "Scissors"(SSRS, Shifted-Subtracted Raman Spectroscopy)*, Raman Spectrocopy, Spectroscopy Europe 14/6 (2002), pp. 1-4.

API—American Poalrizers, Inc., Linear Polarizers, *Near Linear Polarizer—HR*, <http://www.apioptics.com/linear12.htm>, Feb. 3, 2004, pp. 1-4.

\* cited by examiner

PROCESS AND COMPOSITIONS FOR SYNTHETIC CALIBRATION OF BIO-PHOTONIC SCANNERS

BACKGROUND

1. The Field of the Invention

This invention relates to optical measurement of intensity of light and, more particularly, to novel systems and methods for calibrating detectors of Raman scattering.

2. The Background Art

Optical and electronic mechanisms have been developed to generate, detect, observe, track, characterize, process, manipulate, present, and otherwise manage characteristic signals representative of materials, properties, systems, and the like. In the world of engineering, many principles of physics operate predictably, repeatably, and in accordance with the plans and schemes of those harnessing those laws of physics and engineering. Accordingly, over time, the mathematics of analysis or prediction of the performance and behavior of physical systems has been developed to a fine art and a reliable science.

The application of mechanical and electronic apparatus, as well as optical systems, radiation (e.g. radar, light, etc.), and sound (e.g. ultrasonic scanning, sonar, etc.) have proven useful in monitoring many types of systems.

In the biological sciences, instrumentation has proven extremely helpful in both diagnostics and treatments. Likewise, the field of chemistry has benefitted from technology including much instrumentation, including such devices as chromatographs, spectral analysis, and the like.

For example, systems for measurement of selected chemical compositions in biological tissue have been developed in recent years. Useful examples of such apparatus are disclosed in U.S. Pat. No. 5,873,831 issued Feb. 23, 1999 to Bernstein et al., U.S. Pat. No. 6,205,354 B1 issued Mar. 20, 2001 to Gellermann et al., and U.S. patent application Ser. No. 10/040,883 identified as Publication No. US2003/0130579A1 published Jul. 10, 2003, all incorporated herein by reference.

In general, these processes rely on a technique of resonance Raman spectroscopy to measure levels of carotenoids in similar substances and tissue. In certain embodiments, a laser light is directed onto an area of tissue of interest. A small fraction of this scattered light is scattered inelastically by a process of Raman scattering in which energy is absorbed by selected molecules of interest, and is re-radiated at a different frequency from that of the incident laser light. The Raman signal may be collected, filtered, and measured. The resulting signal may then be analyzed in order to remove elastic scattering (e.g. reflectance) of the illuminating source light, as well as background fluorescence in order to highlight the characteristic peak identified as the Raman scattering signal.

In one example, a spectrally selective system, such as a charge coupled device detects radiation (e.g. light waves, photons, etc.) according to intensity and frequency (reciprocally wavelength). Thus, the wavelengths and intensities may be processed in order to quantify the amount of irradiance occurring along a spectrum of frequencies or wavelengths.

The response to impinging, coherent light on tissues may thus be characterized by the amount of energy, the number photons, or the like arriving at a detector in response to a particular illumination source. One can imagine that such a device, if sufficiently precise might conceivably measure even down to an individual photon level of quantum variation in radiant energy response.

In order to implement such devices, a method and apparatus are needed that can reliably calibrate scanners. In operating a scanner, the electrical and electronic artifacts (e.g. errors, characteristics, anomalies, bias, and so forth) of the device in question need to be characterized in order to be factored out of measurements or calculations. Typically, the variations between any two devices produced need to be some how calibrated (e.g. measured, compensated, scaled, normalized, etc.) in order that an output by a particular device be repeatable between devices. Also, two or a hundred devices of a same design need to be able to produce the same or substantially the same value of a detected parameter when evaluating the same subject. That is, the skin of an individual scanned by two or a hundred different machines of the same design should provide substantially the same output value, within some reasonable repeatability (precision) and accuracy (reflection of true reality).

Moreover, inasmuch as conditions change, such as temperature, humidity, chemistry, physical properties, and the like, over short times and long times in some expected, unexpected, predictable, or unpredictable manner, a machine needs to be calibrated to remove its own temporal (time wise) variations in operation. That is, a method and apparatus are needed to calibrate a scanner in such a way as to factor out the vagaries of physics, chemistry, temperature, external conditions, and the like that may otherwise affect the output of a device. Thus, a method and apparatus for factory and field calibration for a bio-photonic scanner would be an advance in the art.

To the extent possible, it would be an advance in the art to establish a process for processing signals received from a scanning device, in order that the hardware not be required to any performance parameter, physical characteristic, or other control parameter associated with a scanning device. Thus, it would be an advance in the art to develop signal processing or computational processing of signal data obtained from a scanner in order to provide all the foregoing calibration benefits.

Biological materials are inherently highly variable. Moreover, the portability, degradation, etc. of a sample may be problematic. For example, how does one normalize or calibrate two different machines on two different continents scanning two different populations in order that those devices read the same.

Calibration samples taken from biological materials are inherently problematic. Biological tissues are either in vivo or not. In either event, the amount of a sample, the repeatability of a sample, the control and observable characteristics of a sample are nearly impossible to maintain when dealing with biological materials. Moreover, the replication of biological materials, organisms, tissues, or other substances is extremely difficult. Moreover, the variation in conditions cannot be precisely controlled in many circumstances. Providing identical conditions, genetics, and the like in an organism is not a practical mechanism for generating calibration samples.

Thus, what is needed is a synthetic material that can be generated, manufactured, or otherwise produced by a predictable set of standards, with some processing that can be repeatably controlled, in order to provide a sample for calibrating a scanner. That is, what is needed is a synthetic material or a system of synthetic materials that can be relied upon to produce and maintain over an extended period of time a consistent radiant response when illuminated by a scanner. Accordingly, such synthetic materials may then be used to establish calibration standards that can be transported and verified worldwide.

Moreover, even within the context of a factory, having a stable, repeatable, reproducible, easily manufactured synthetic sample that can be used to calibrate machine-to-machine variations out of the performance of those machines would be extremely valuable. Moreover, some type of field calibration apparatus and method, particularly if including a reliable synthetic material as a sample, would be a substantial advance in the art in calibrating out the day-to-day or time-to-time variations in the output of an individual scanning apparatus and associated processor.

BRIEF SUMMARY AND OBJECTS OF THE INVENTION

In accordance with the foregoing needs, a system of various apparatus and methods is disclosed herein for calibrating bio-photonic scanning systems. Moreover, synthetic materials have been discovered, formulated, evaluated, and otherwise made available to perform the various calibration functions required of a bio-photonic scanner. For example, a dark cap for returning substantially no radiant response to a scanner, in response to laser illumination, provides for a mechanism to factor out the electrical and electronic artifacts of the machine. Similarly, a white scan sample has been developed that replicates the shape and values of the spectral response of biological tissues, while being reproducible as a simple non-biological chemical composition.

Moreover, materials have been discovered and developed for doping a matrix of material in order to present synthetic mimics of certain molecular structures of interest.

For example, carotenoids and other chemical compositions existing in biological tissue appear to contain certain, characteristic, carbon, double-bond structures. Synthetic materials have been discovered that contain similar bond structures, responsive to illumination by providing a radiant response (e.g. Raman scattering, etc.) similar to that of biological molecular constituents. Accordingly, a system and method have been developed to implement synthetic materials as calibration samples in order to calibrate scanning systems repeatably. Moreover, the various compositions and apparatus developed and discovered have been implemented successfully in a series of calculations and mathematical manipulations of data in order to process the output of a scanner, normalizing and otherwise neutralizing undesirable or uninteresting characteristics of spectral curves of radiant intensity. Thus, machine-to-machine variations as well as time-to-time variations within a single machine can be factored out, yielding much better signal to noise ratios and much more evident Raman responses. Accordingly, proper calibration apparatus and methods provide for accurate and repeatable utility of bio-photonic scanner.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE ILLUSTRATED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 12, is not intended to limit the scope of the invention, as claimed, but is merely representative of certain presently illustrated embodiments of the invention.

The various embodiments in accordance with the invention will be best understood by reference to the drawings, wherein like parts are designated by like numerals throughout.

Figure 1:
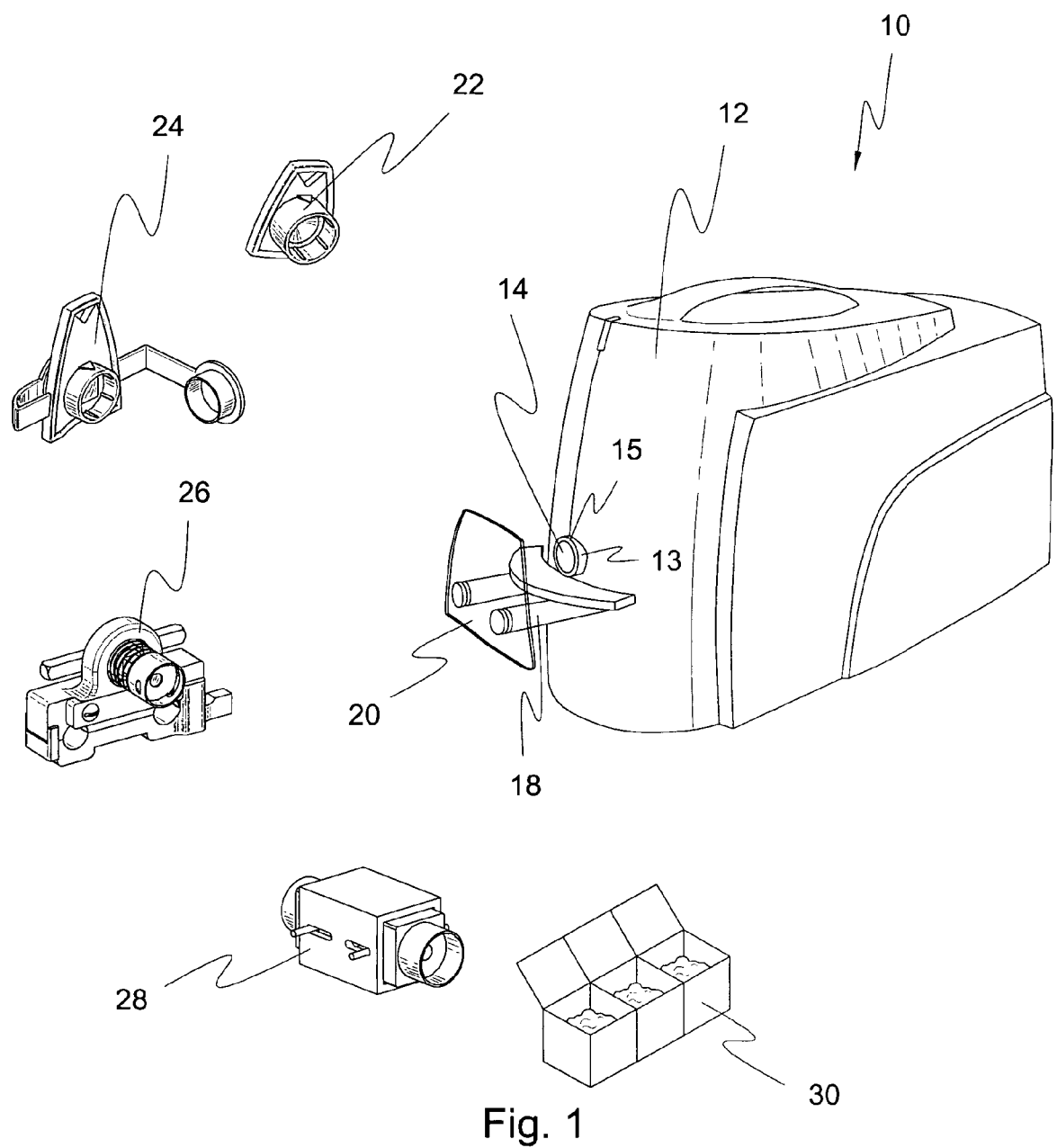
FIG. 1 is a perspective view of one embodiment of an apparatus in accordance with the invention including several mechanisms for presenting scanning samples during calibration processes.

Referring to FIG. 1, an apparatus 10 in accordance with the invention may include a scanning mechanism including a power supply, a light source, such as a laser light source, and a detector. The detector may receive signals including background fluorescence, elastically scattered light (reflections of source light), as well as Raman-scattering light returning to the detector at a wavelength different from that of the incoming illumination beam.

In general, the scanning mechanism will be enclosed within a housing 12, having a barrel 13 penetrating therethrough in order to deliver both illumination and returning detectable beams therethrough. Typically, a barrel 13 may be provided a certain amount of relief or clearance radially between the barrel 13 and the housing 12.

A window 14 mounted in the barrel 13 passes an illuminating beam outward to a subject, and a return "radiant response" back through the window 14 to be received by a detector. For example, a charge-coupled device (CCD) or charge-injection device (CID) may constitute an array of sensors capable of detecting light of various frequencies (e.g. and corresponding wavelengths). Accordingly, a histogram or spectrum of intensities may be displayed over a domain of frequencies or a domain of corresponding wavelengths.

In one embodiment of an apparatus 10 in accordance with the invention, a rest 16 is positioned below and outwardly or in front of the window 14. Supports 18 may extend from the apparatus 10 within the housing 12 to support the rest 16. Accordingly, a hand, arm, or other member of a subject may be positioned on the rest 16 in front of the window 14.

In one presently contemplated embodiment of an apparatus 10 and method in accordance with the invention, a hand of a user is positioned on the rest 16, placing the skin of the palm of the hand against the window 14. In this way, distance effects, as governed by Bier's law are repeatably controlled by the position of the window 14.

A shield 20 may provide several functional features. For example, in one embodiment, the shield 20 is formed of a translucent material shining in response to a beam of light output through the window 14 from the apparatus 10. Light passing through empty space has no mechanism to render it visible outside of the beam itself. Accordingly, as a matter of safety, laser light may be intercepted and scattered by the shield 20. By the same token, a user may be notified that the apparatus 10 is powered up and operating by the visibility of a spot of light illuminating the shield 20.

In various embodiments, the shield 20 may be clear, translucent, textured, or simply otherwise formed to diffuse light randomly. In certain embodiments, the shield 20 may be opaque.

In yet another embodiment, a diffusion layer of a material, such as, for example, linen or the like, may be embedded within layers of transparent or translucent polycarbonate in order to provide substantial diffusion.

Various functional features of the apparatus 10 may be served by a series of accessories such as a dark cap 22 or a dark sample 22 returning no significant beam to the apparatus 10 in response to illumination received from the window 14, corresponding to substantially no radiation (e.g. light) of interest. This signal represents spurious contributions to the apparatus 10 as a direct result of the electrical or electronic artifacts (e.g. errors, background noise, etc.) of the apparatus 10 itself.

Precision samples 24 may be embodied in a film cap 24, sometimes referred to as a field calibration cap 24. The cap 24 may be placed over the window 14 in either a low value or a high value position, resulting directly from two different material samples in opposite sides of the precision cap 24 or the two different distances of a single material therein.

A loaded cap 26 provides a mechanism that can be repeatably and stably mounted to the supports 18 in order to provide spring-loaded positioning of a test sample against the window 14. Similarly, a double cap 28 or a test block 28 having spring-loaded caps on both ends, each with a sample, producing a high or low value, is shaped and sized to be positioned between the window 14 and the shield 20.

The master samples 30 comprise moldable materials that may be temporarily adhered to the window 14 to replicate synthetically the scanning of a bodily member such as a hand. For example, the master samples 30 are structured to be positioned as a putty-like material adhered to the window 14 to produce or appear as neutral background (white scan) results, comparatively low concentrations of molecular compositions of interest and comparatively high concentrations of molecular compositions of interest. The molecular composition of interest is distributed within the putty of the master samples 30 in accordance with the comparative value of the concentration of the molecular constituent of interest desired.

Figure 2:
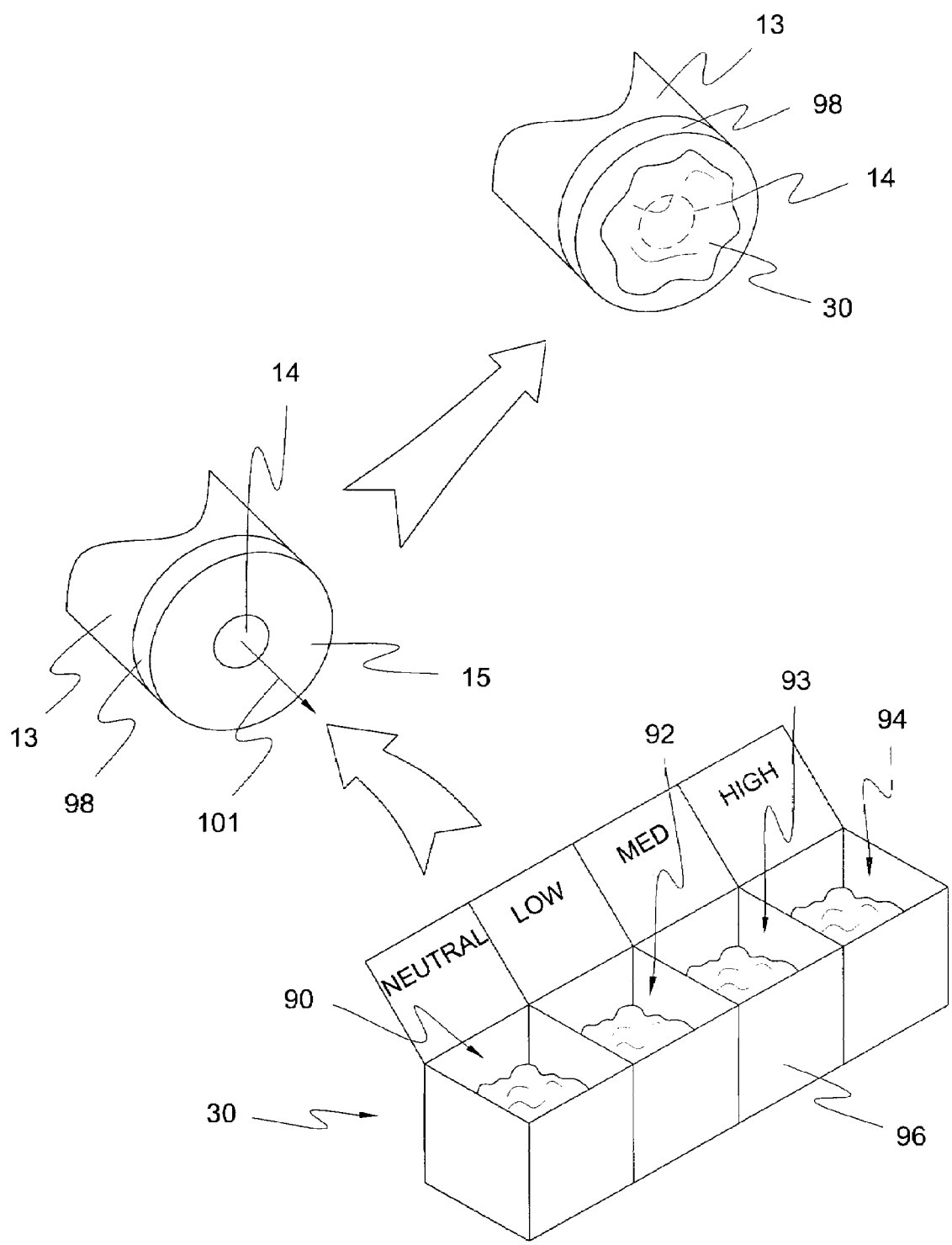
FIG. 2 is a perspective view of a window and barrel portion of the probe of a scanner, together with the master sample system and installation thereof during calibration of a scanner using a synthetic mimic material to replicate the radiant response of tissues.

Referring to FIG. 2, a master sample 30 may actually include a neutral sample 90, a low-valued sample 92, one or more medium-valued samples 93, and a high-valued sample 94. Having these samples 90, 92, 93, 94 properly labeled case 96 provides a set of standards by which a factory calibration can substantially neutralize machine-to-machine variations in performance. That is, the master sample 30 or sample set 30 provides calibration standards to assure that each apparatus 10 produced will provide a substantially equivalent reading on the same sample material.

A master sample 30 may be adhered to the face 15 and window 14 directly. Typically, the window 14 is secured to or within the barrel 13 by some mechanism, such as a collar 98 or other internal registration mechanism. Accordingly, the window 14, itself, determines the actual positioning of the sample 30.

The thickness of the sample 30 should be sufficient to preclude any transparency or translucence. Likewise, the sample 30 should cover the window completely to preclude ambient light. By the same token, a hand, arm, or other member of a subject may likewise be placed in direct contact with the window 14 in order to provide a proper preclusion of ambient light as well as distance registration of the subject for testing.

Applicants have discovered that the master sample 30 may be effectively formed of a polymer composition. In one presently contemplated embodiment, a material identified as Dow Corning 3179 dilatant compound has been found highly effective to replicate certain properties of human tissues extremely efficaciously. A pigmented version of such material is available under the Crayola™ brand and seems to work even better. In general, pigmented material comprising silicone oil cross linked by boric acid has been found very effective to provide a similar reflectance or elastic light scattering, as well as similar fluorescence, compared to those detected from human skin.

In one presently contemplated embodiment, the master sample set 30, and in particular the neutral sample 90 or white scan sample 90 may include dimethyl siloxane. These are hydroxy-terminated polymers with boric acid. In addition, silica as crystalline quartz may be added to the composition, as well as a proprietary thickener. The thickener is identified by the manufacturer brand name as thixotrol ST. The pigment is the standard flesh tone used in commercial toys, such as, "Silly Putty™."

Other silicone compositions included are polydimethylsiloxane as well as a trace of decamethyl cyclopentasiloxane. A similar amount of glycerine and titanium dioxide may be added to the composition.

In one presently contemplated embodiment, the master sample 30, and particularly the matrix that forms the neutral sample 90 contains approximately 65 percent dimethyl siloxane, 17 percent silica, nine percent thickener, four percent polydimethylsiloxane, one percent decamethylcyclopentasiloxane, one percent glycerin, a percentage of pigment to maintain opacity, and one percent titanium dioxide. The matrix material that forms the neutral sample 90 may be characterized as a viscoelastic material. That is, the material 90 responds elastically in response to high rates of strain (e.g. impact), and responds as a liquid in response to comparatively very low rates of stress and strain (e.g. its own weight).

In order to provide the low-valued sample material 92 and the high-valued sample material 94, a doping agent or dopant may be mixed into the neutral sample 90. Naturally occurring or "organic" materials from biological sources have been found effective. For example, foodstuffs containing high values of carotenoids may be comminuted (e.g. pulverized, ground, etc.) and mixed into the matrix material 90. Tomatoes, carrots, vegetables, fruits, and the like containing suitable values of carotenoids can be substantially mixed or dissolved within the matrix 90 in order to produce the samples 92, 94.

Synthetic liquids and solids, as well as organic liquids and solids that will mix well may dope the putty. Applicants have also discovered that synthetic materials exhibiting the carbon bonding behaviors of carotenoids may, for example, be ground, milled, or otherwise comminuted and dispersed into the matrix material 90 in order to produce the low to high valued samples 92, 93, 94.

The value of a low, medium, and a high value samples 92, 93, 94 may be ascertained by testing a wide range of samples of human subjects. Thereafter, a suitable amount of dopant may be added to the matrix 90 in order to provide suitable values representing comparatively high to comparatively low ranges of radiant response corresponding to those of human tissues in vivo.

The master samples 30 provide great utility inasmuch as they can be repeatably compounded from synthetic materials to provide very stable results. To the extent that radiation (e.g. light) may affect the molecular bonds in a material relied upon for testing and calibration, the matrix 90 may be molded to expose different particles. That is, the matrix 90 being a moldable plastic or viscoelastic material may be molded or kneaded in order to thoroughly and evenly disperse the selected amount of dopant.

By the same token, to the extent that a dopant material may alter its chemical structure as a result of continued or prolonged radiation, the master samples 30 may be kneaded in order to redistribute dopant and provide a continuing, substantially constant value of the radiant response therefrom in response to illumination from the window 14 of the apparatus 10.

Calibration with synthetic materials is also appropriate to work out various conditional variations. For example, temperatures, humidity, electronic drift, and the like may alter the operation of the components of an apparatus 10. Accordingly, with each startup of a scanning session, or even after an extended period within a single scanning session, calibration of the apparatus 10 may be appropriate. The master samples 30 have been found to operate when re-used up to 50 times without degradation, if kneaded again after each long exposure (e.g. ten minutes of laser light) to light from a scanner 10.

Figure 3:
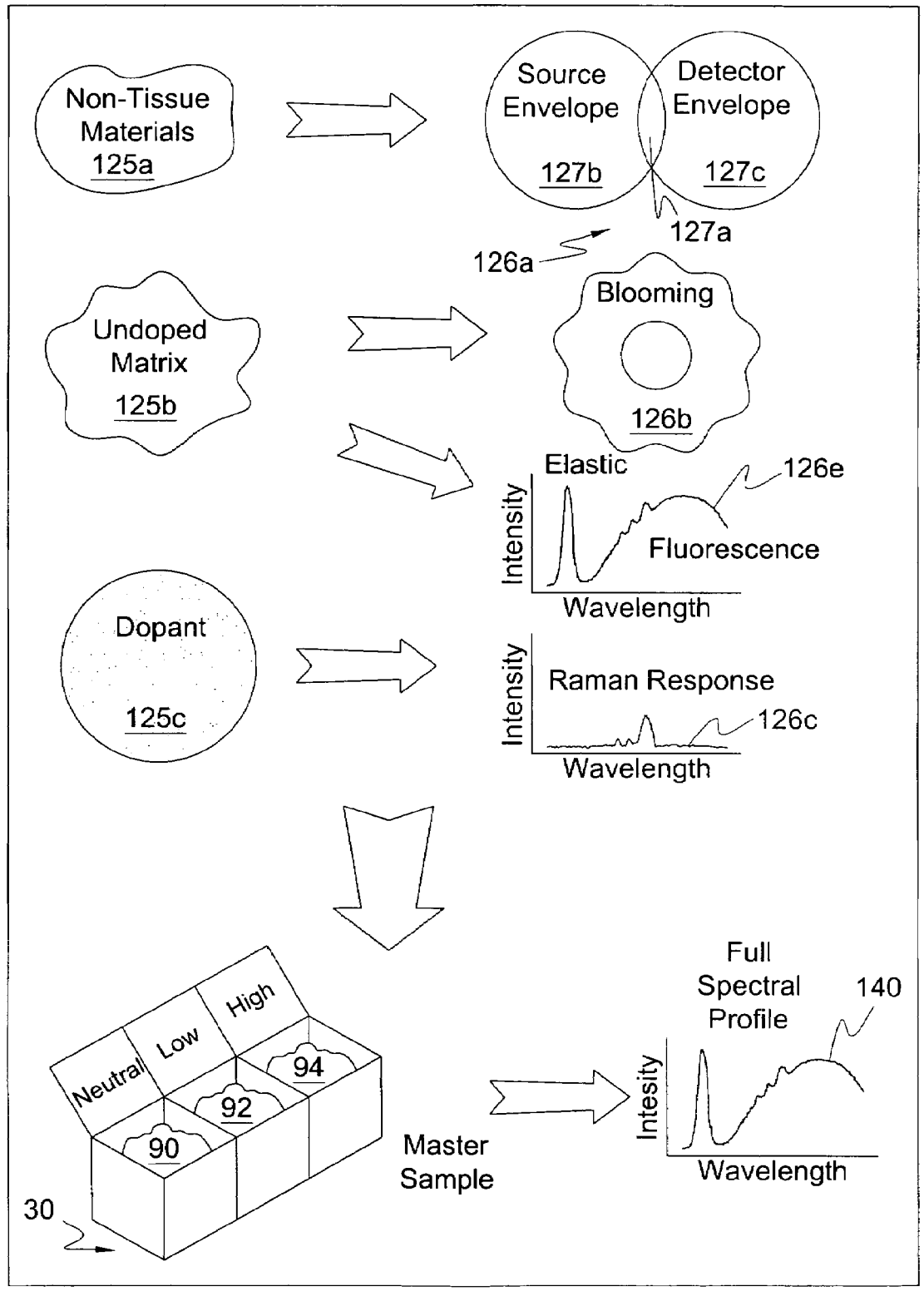
FIG. 3 is a schematic diagram illustrating the relationships between synthetic and other non-tissue materials useful in operation of an apparatus and method for calibration in accordance with the invention, including undoped synthetic matrix materials, dopants, with the resulting master samples and selected radiant response characteristics of the foregoing.

Referring to FIG. 3, applicants have observed that non-tissue materials 125a when exposed to a beam 101 from a window 14 of an apparatus 10 may result in comparatively clearer and well-defined shapes 126a. An area 126a of intersection may place either region 127b, 127c inside the other 127c, 127b or offset as illustrated. The intersection 127a may be substantially less than the area or size of a source envelope 127b representing the area of illumination from the beam 101 proceeding from the window 14. Likewise, the area 127a of intersection may be substantially less than, and misaligned with the area 127c of the detector envelope 127c.

That is, the center of the region illuminated by the source, the source envelope 127b, and the region that is "read" by the detector in the apparatus 10, the detector envelope 127c may be misaligned. The area 127a may therefore be insufficient to be representative of the real radiant response of a sample, calibration material 30, or the like.

By contrast, human skin and the undoped matrix 125b (the neutral material 90 from the master sample set 30) provide a blooming response 127b. Rather than the clearly defined envelopes 127b, 127c that occur in many other materials, human skin as well as the undoped matrix material 125b of the neutral sample 90 or white scan sample 90 of the master sample 30 provide a blooming shape 126b. This blooming shape 126b may be thought of as an enlarged area of radiant response, reflection, scattering, and the like in a highly spread shape 126b. The blooming shape 126b or effect 126b results in a much better intersection 127a between the source envelope 127b and the detector envelope 127c.

Thus, the undoped matrix 125b (e.g. material 90) represents comparatively accurately the behavior of human skin, absent the Raman scattering effect due to carotenoids or other materials containing similar carbon bonds. A curve 126e reflecting the elastic scattering portion and the fluorescence of skin, may be achieved by using the undoped matrix 125b as a calibration sample.

In contrast, dopant materials 125c, such as naturally occurring materials or synthetic materials having the proper carbon bond structures to mimic the behavior of carotenoids or other molecular structures of interest provide a curve 126c identified as a Raman response. Thus, the peaks, and particularly the highest peak typically found at 510 nanometers wavelength, result from illumination of a dopant 125c by the light illuminating test samples 30, 50 from the window 14 of the apparatus 10.

Applicants have discovered that compounding a dopant 125c into the matrix 125b provides the master samples 30 capable of substantially replicating the behavior of human skin reliably and repeatably. The curve 140 of intensity as a function of wavelength obtained by illuminating and reading (e.g. scanning) the master sample 30 provides the full spectral profile 140 expected from the skin of a subject. The neutral sample 90 comprised of the undoped matrix 125b provides a curve 126e capable of identifying, and therefore neutralizing out, the effects of elastic scattering of illuminating light, as well as the skin's natural fluorescence. Meanwhile, different concentrations of doping in the low value sample 92 and the high value sample 94 of the master sample 30 provide comparatively different curves 140 and particularly the Raman response curves 126c contributing thereto.

Figure 4:
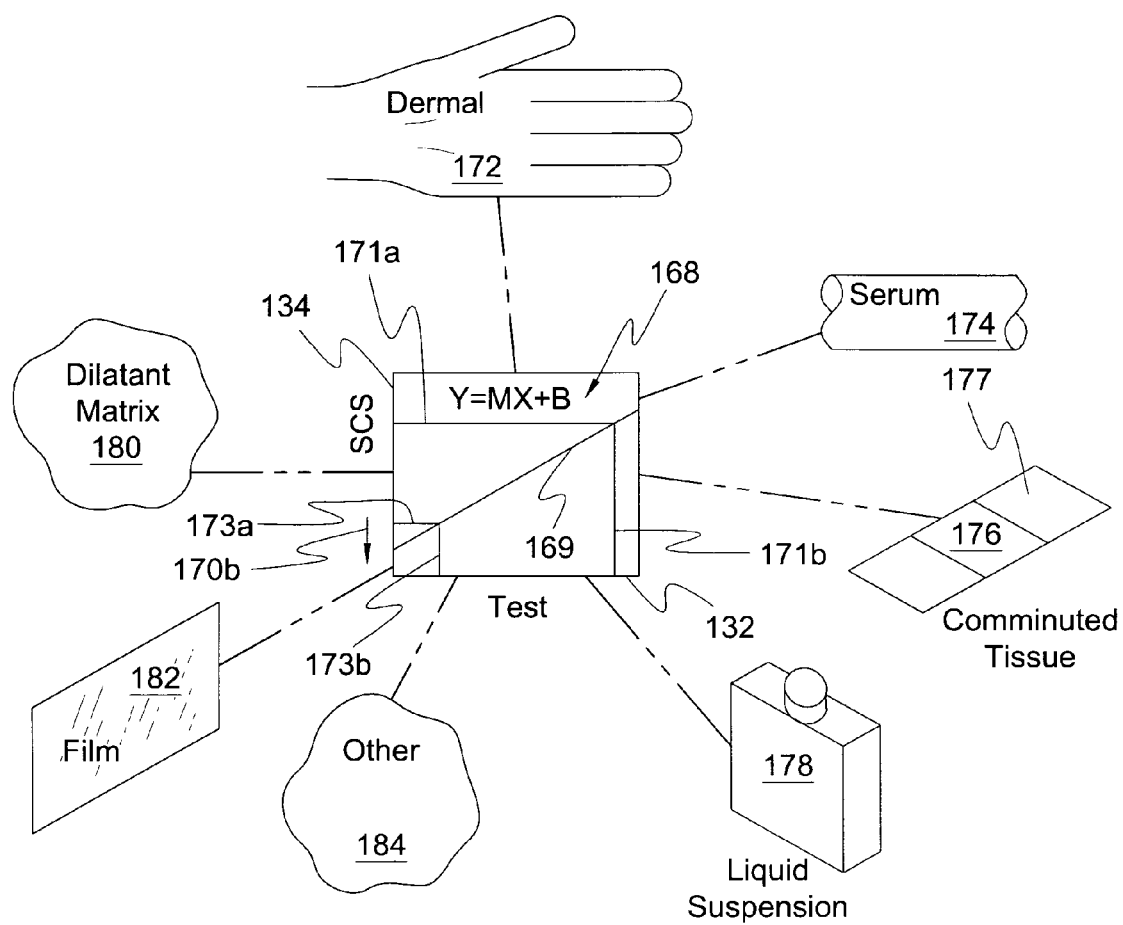
FIG. 4 is a schematic diagram illustrating various material compositions and formats that can be scanned or otherwise evaluated to obtain raw data, radiant responses, or calibration curves, along with a schematic chart for scaling the calibration of an individual scanned result to the scale of a particular standard for scanning results.

Referring to FIG. 4, an equation 168 representing a mapping of scale. A particular standard may be established against which other apparatus 10 may be calibrated, including being scaled. A laboratory unit or other device may be established as a standard. The numerical count (range, intensity, output, etc.) provided by the system or apparatus 10 corresponds to intensity, a function of the number of photons impinging on a detector at a particular frequency and wavelength. Early devices bordering on laboratory curiosities were sufficiently sensitive to provide almost a count of photons. Thus a single count on a scale of zero to 67,000 was actually close to a count of photons impinging on a detector as a result of a scan.

The apparatus 10, need not be so sensitive as to accommodate and register arrival of every photon, so long as a measure of intensity is accurate and repeatable. Each apparatus 10 needs to read a given sample (e.g. master samples 30, live subject, etc.) and output a score or number identifying the same value for intensity of light detected. Thus, each apparatus 10 needs to be calibrated to match a standard. The advent of the synthetic master sample set 30 provides such a standard. This standard or master sample 30 is more reliable than data taken on biological samples, such as people or plant materials, since it is not subject to the vagaries of biological processes and degradation.

In FIG. 4, a skin carotenoid score SCS is a score or number corresponding to a reading achieved as an output of an apparatus 10. In calibration, this is the value output from reading the master sample 30. This is represented on the range (vertical) axis. The domain axis represents a value corresponding to the Raman scattering intensity obtained by a machine 10 under calibration to that same standard (e.g. a master sample 30).

A line or curve may be defined by the peak heights responding to scans conducted on the low to high samples 92, 93, 94. The high sample 94 must read at the high value selected, (e.g. for example 67,000 in one embodiment) and the low sample 92 must read at the low value selected (e.g. at 21,500 in one embodiment). Other scales of numbers may be used, as discussed above, but these serve as one example.

Any resulting peak height 150 obtained on a machine 10 after calibration may be adjusted by a line of FIG. 4, mapping the output range of that calibrated machine to a set of standard values obtained from the same samples on a standardized test (e.g. apparatus). The map is made, resulting in a mapping equation during factory calibration. In one embodiment, a coefficient (representing a slope M) and a signal subtract (corresponding to an intercept B) may be used to obtain the readout value (corresponding to dependent variable y) for any input readout value (independent variable x) from the calibrated scanner.

Thus any resultant peak height obtained during a scan conducted by the calibrated machine 10 is scaled to the standard. This may be sufficiently accurate with only two points required for calibration, since Raman scattering is a linear effect. Accordingly, more points and higher order equations or terms are not required but could be used in order to map calibration scales of machines.

In practice, a dermal subject 172 is typically the palm of the hand of a person. Meanwhile, the content of molecular structures in serum 174 (e.g. bloodstream) in users can be correlated to samples 30.

Previously, laboratory developers of Raman scanning spectroscopy for carotenoid content could rely on comminuted tissues 176 from cadavers. Setting and fixing slides 177 is inherently subject to a lack of sample supply and repeatability for field calibration. Subject to irradiation, a factory sample has sufficient repeatability problems of its own. Irradiation sometimes affects the chemistry of carotenoids. Therefore, a repeatable, stable, sample from such a source is unlikely and difficult.

Accordingly, applicants have used cuvettes filled with a liquid suspension 178 of synthetic materials, organic materials, and the like. The distance of the sample from the window 14 is problematic. Providing an opaque liquid suspension 178 helps solve that problem.

In fact, the dilatant compound matrix 180 (e.g. the neutral sample 90 of the master sample 30, or the undoped matrix 125b) provides the needed opacity, and is technically a liquid. The viscoelastic material flows under small force, albeit slowly. The use of film 182, been found to be stable, predictable, and very useful, although, the oriented nature (e.g. polarizing function) of these oligomeric films 182 limits their use.

Other materials 184 may also be used. Nevertheless, opaque materials tend to be preferable, or at least materials that are sufficiently solid and responsive to fix distance effects. For example, as discussed hereinabove, samples 50 formed of film materials 182 can be used at different distances to represent different radiant responses, as if the distance were instead the molecular structure of interest at a different concentration.

Figure 5:
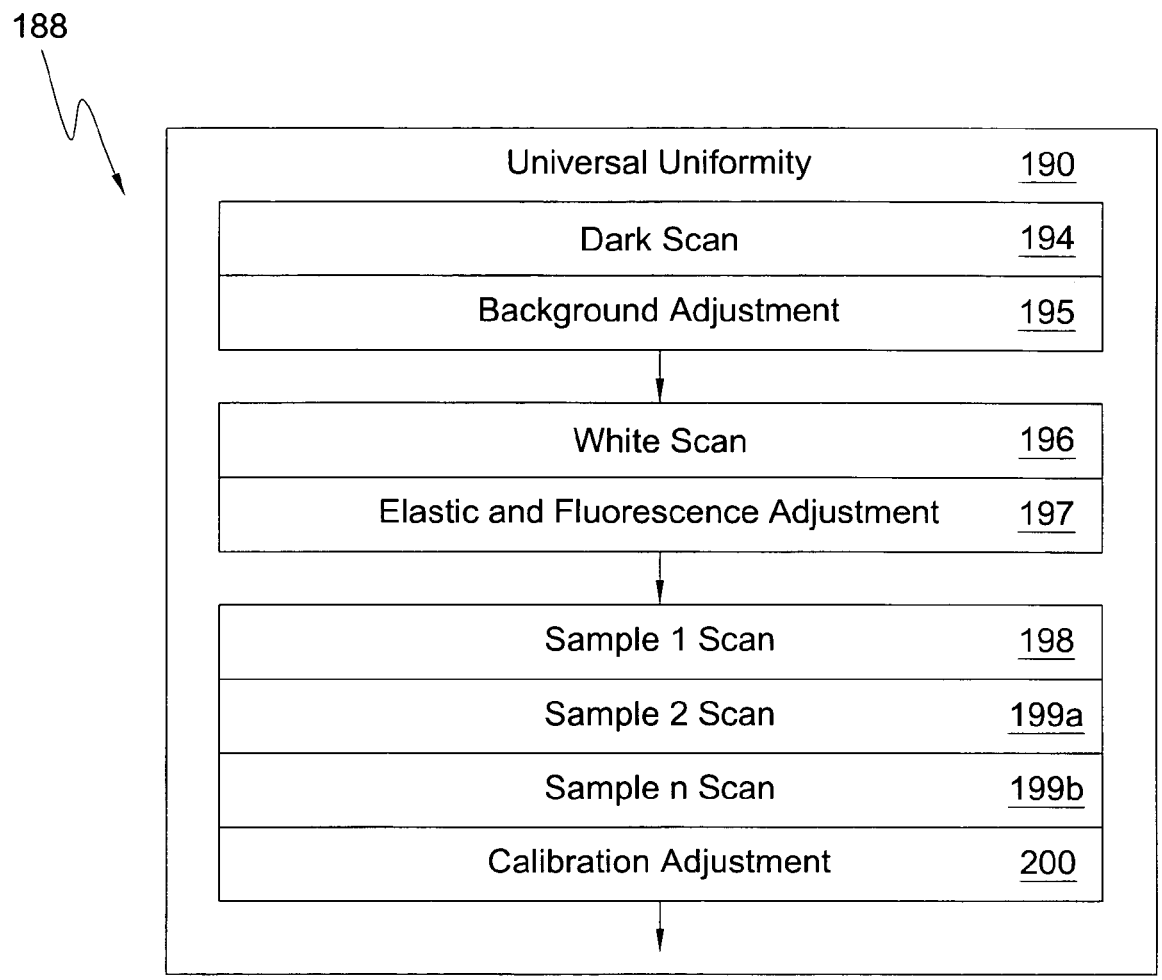
FIG. 5 is a schematic block diagram of one embodiment of a process for calibration relying on synthetic or other master samples to obtain unit-to-unit uniformity, as well as condition-to-condition uniformity over time for a scanner and calibration system in accordance with the invention.

Referring to FIG. 5, a calibration process 188 may be thought of as a uniformity control process 190. As described hereinabove, a dark scan 194 may be followed by a background adjustment 195 of the controlling parameters associated with the apparatus 10, and the software processed in the CPU associated therewith, regardless of whether or not the CPU is embedded in or remote from the apparatus 10. Similarly, a white scan 196 results from an illumination of the neutral sample 90 by a beam 101, with collection of the radiant response therefrom. Accordingly, the resulting data may be used to make an adjustment 197 to the elastic and fluorescent portions of the data curve 140.

A series of sample scans 198, 199 comprising low to high valued samples 92, 93, 94 provided data points on which a calibration adjustment 200 may be made. The apparatus 10 and data processing are adjusted to provide an output therefrom matching a standard value for each sample 92, 93, 94.

Figure 6:
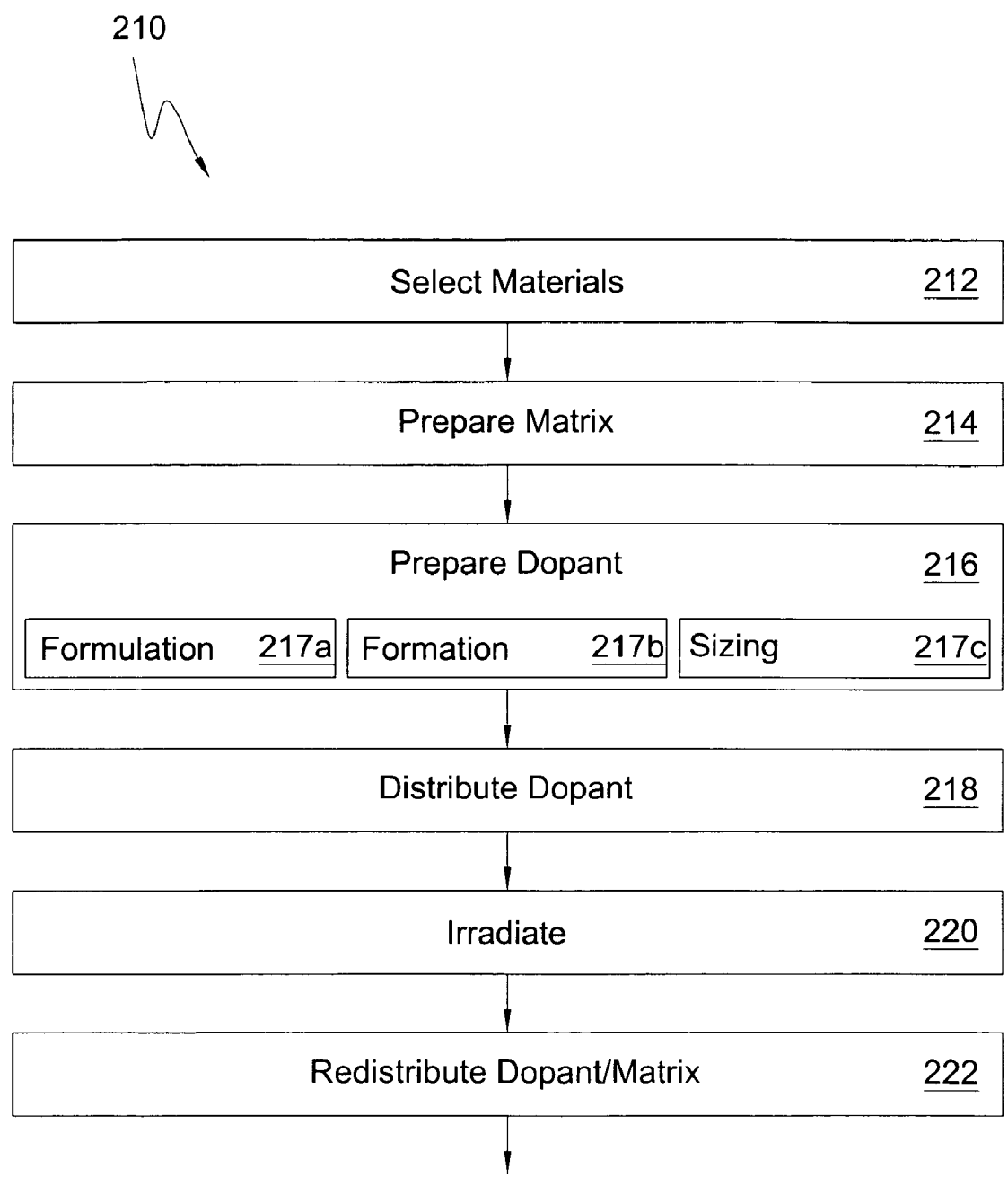
FIG. 6 is a schematic block diagram of a process for formulation and use of a master sample for calibration of a scanner in accordance with the invention, applicable to naturally occurring materials dopants as well as fully synthetic matrix and dopant materials.

Referring to FIG. 6, a process 210 for creating master samples 30 may include selecting materials 212. This may include selection of a suitable material for a matrix 125b, as well as a suitable dopant 125c. By the same token, multiple matrices 125b, or multiple constituents for a single matrix 125b may be selected. Likewise, one or more dopants 125c may be selected for compounding and distribution or suspension in the matrix 125b.

After selection 212 of materials, including suitable testing, and other evaluations, preparation 214 of the matrix 125b may be done to order. This may be done by a supplier capable of delivering repeatable batches of the matrix material 125b.

Preparation 216 of dopants may include, for example, formulation 217a of a proper chemical or molecular structure of interest. Likewise, formation 217b of such a dopant 125c in a suitable format may be required. For example, suitable dopants of HCL-reacted PVA, ground to pass through a chemical processing sieve worked well and repeatably at all proportions of interest in samples 92, 93, 94. Organic liquids have been shown to work, although liquid synthetic resins have not yet been used directly for doping.

Formation of particulate matter may include mechanical structuring of the particles, sizes, and the like. Sizing 217c of 200 mesh to over 325 mesh works, but higher mesh does not improve results. Ultimately, distribution 218 of the dopant 125 in the matrix 125b results in a full set of master samples. That is, the neutral sample 90 comprises an undoped matrix 125 in one embodiment. Likewise, the low, medium, and high samples 92, 93, 94 will typically involve different concentrations of dopant 125 calculated and tested to provide a particularly suitable and broad range of values ranging from the higher to lower ends of the expected results. For example, a low value will typically be 18,000-25,000, a medium value will typically be from about 38,000 to about 52,000, and a high value composition 94 will typically register from about 56,000 to about 78,000. These values actually originally corresponded to phantom counts received by very sensitive, prototype detector. On such a scale, human subjects have been scanned and found to typically lie between readings of twenty thousand and fifty thousand. Outliers may exist above and below this range, nevertheless.

In certain embodiments, a calibrator contains a sample comprising a mimic material selected to mimic the radiant response of tissue. Determining a calibration parameter for the scanner may involve directing light from the illuminator onto the mimic material and detecting a first radiant response thereto. Inputs to the processor corresponding to a state of the light, the first radiant response to the light, and the calibration parameter enable calibration. Inputs are processed to repeatably detect a second radiant response of tissue in vivo as a result of exposure to light from the illuminator.

The method may include determining a calibration parameter, including selecting a curve corresponding to errors attributable to electrical artifacts and optical artifacts of the scanner to be corrected out of the radiant responses. The method may also include selecting a filtering parameter to filter out elastic scattering from radiant responses.

Selecting a curve corresponding to background fluorescence permits correction of this feature out of radiant responses. Points to define a curve corresponding to a radiant response, absent a Raman scattering response of interest therein may isolate a Raman scattering response of interest.

Typically, the light is coherent light from an illuminator such as a laser and the radiant response is an intensity corresponding to a selected molecular structure of the tissue, a constituent of interest, such as carotenoid materials, antioxidants, vitamins, minerals, amino acids, or the like. A Raman scattering response corresponding to carotenoids has been found effective. Moreover, calibration scans may be done using "mimic materials" of non-animal-tissue materials, structured to provide distinct readings different from one another. Different intensities can also be achieved for calibration by positioning one type of material at two different and distinct distances from the detector.

Samples found effective include various polymers, synthetic materials such as long chains, and oligomers. For example, samples include a pliable matrix containing a selected quantity of a dopant in different concentrations. The dopant may be a solid powder, a liquid, a synthetic, or a naturally occurring material. A powdered dopant sized to pass through about a no. 200 sieve has been found to form a good dopant. About a number 300 or greater sieve size is better, but no noticeable improvement appears with pure dopant above a sieve number of about 300.

A matrix of pigmented dilatant compound doped at two or more concentrations of dopant can receive naturally occurring material or a synthetic material. Effective synthetic materials seem to include a carbon-to-carbon bond corresponding to a similar bond in carotenoids.

Determining calibration parameters may include calculating correction curves to combine with data curves corresponding to the radiant responses of test (calibration) materials in order to isolate a "carotenoid" type of response therein. The correction curves may include data corresponding to at least one of elastically scattered light, fluorescence, and background artifacts of the scanner.

For calibration a bio-photonic scanning machine is provided with a "dark cap" for collecting dark data in which substantially no light of interest returns to the detector, the dark data representing electrical artifacts of the scanner. Adjustments may be made according to the intensity of light from the illuminator, the response of the mimic material used in calibration, and correlation of the radiant responses of samples having different concentrations of dopants. The radiant responses to dopants are correlated between the sample and tissue in vivo.

In one embodiment, an operator may operate the scanner in a feedback control loop to detect in a subject an initial level of carotenoids in tissue. The subject may then ingest nutritional supplements according to some regimen over a subsequent period of time. Later testing with the scanner detects a subsequent level of carotenoids in tissue corresponding to the administration of the nutritional supplements.

Calibration of a scanner connected to a computer having a processor and memory may isolate a Raman response of carotenoids from elastic scattering, fluorescence, and electrical and optical artifacts of the scanner. A first synthetic material may be scanned to provide a "white scan" representing a portion of the radiant response of tissue attributable to optical artifacts of the scanner, reflected light, and re-radiated light at wavelengths not of interest (e.g. fluorescence). A suitable synthetic material is a viscoelastic material originally formulated by Dow Chemical and known as dilatant compound. In addition to serving as a neutral sample for conducting a "white scan" of background radiant effects, the dilatant compound may be doped at various concentrations.

In one embodiment of a system and method in accordance with the invention, a scanner of a bio-photonic type detects selected molecular structures of tissues, nondestructively, in vivo, from radiant responses of tissues to illumination by light from the scanner. The calibration system may include a dark sample returning a dark response corresponding to electrical artifacts of the scanner and comprising substantially no radiant response upon illumination thereof by the light. A white sample includes a first synthetic material returning a white response, upon illumination thereof by the light, substantially corresponding to a radiant response to the light of tissue, absent a characteristic Raman scattering response of interest.

A high valued sample may be formed of the first synthetic material treated with a dopant to return, upon illumination thereof by the light, a high response value corresponding substantially to a comparatively higher value of a radiant response of tissue to the light. A low valued sample may be formed from the first synthetic material treated with the dopant to return, upon illumination thereof by the light, a low response value corresponding substantially to a comparatively lower value of a radiant response of tissue to the light. The dark, white, high, medium, and low samples are each selected, formulated, and formed to provide parameters, which in mathematical combination calibrate the scanner, controlling computer, or both to provide a repeatable value of an output corresponding to molecular content in tissue in vivo in response to the light.

The basic synthetic material (e.g. matrix) is optically opaque, viscoelastic, silicone-based compound. It may include dimethyl siloxane, crystalline silica, a thickener, pigment, and polydimethyl siloxane as principle constituents. Decamethyl cyclopentasiloxane, glycerine, and titanium dioxide may be present in comparatively small amounts, and even a little water (e.g. 10-30, or about 20 grams per kilogram). The silicone chains are hydroxy-terminated polymers cross-linked by boric acid.

Dopants may be naturally occurring materials (e.g. carotenoids originating in plants, vegetables, foodstuffs, etc.) or a synthetic material. Synthetic materials having a molecular bonding structure corresponding to characteristic molecular bonding found in carotenoids seem to serve the purpose. One dopant is found to contain a chain of carbon bonds, including characteristic carbon-to-carbon double bonds. As a finely comminuted solid, the dopant suspends in the silicone-based matrix to mimic the Raman scattering and other radiant response properties of skin.

An apparatus for calibrating a scanner of a bio-photonic type may include hardware such as a dark scan structure, a factory calibrator of a standardized set of synthetic materials at different levels of doping, a field calibrator of a polarizing film, and a software executable in a computer-readable medium to receive and process data corresponding to scanning the dark scan structure, the factory calibrator, and the field calibrator. A computer programmed to run the executable calibrates the scanner and operates to control the scanner and output a value corresponding to the amount of the selected molecular structure based on data acquired during non-destructive scanning of tissue of a subject.

Figure 7:
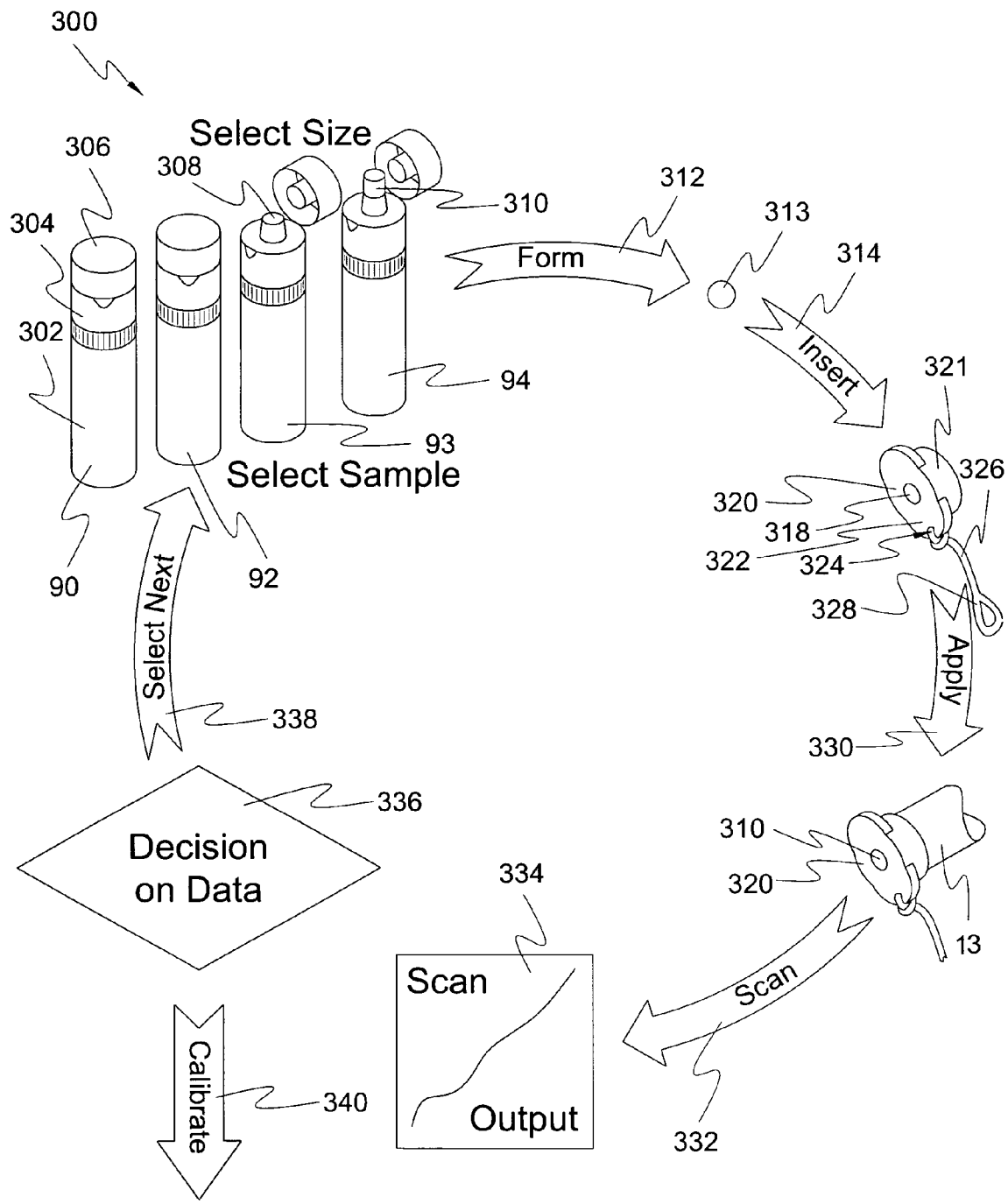
FIG. 7 is a schematic block diagram of a method for field operation and calibration of a scanner and calibration apparatus and method in accordance with the invention.

Referring to FIG. 7, a process 300 for establishing the calibration of a photonic scanner 10 may involve the use of tubes 302 containing a material for calibration. In one embodiment, each tube 302 may include a collar 304, driver 304, or the like to urge calibration material out of the tube 302. Each tube 302 may be provided with a lid 306 having an aperture 308 formed therein. The aperture 308 may size a sample 310 extruded therefrom upon rotation of the collar 304.

In one embodiment, the sample 310 may be formed 312, typically kneaded to an approximately round shape. For example, an operator may knead an approximately ¼ inch ball of putty-like material for approximately 15 seconds. This forming process 312 may somewhat warm the sample 310 and provide additional mixing thereof. Thus, forming 312 by kneading, rolling, or some combination thereof, may provide a ball 313 that may be inserted 314 into a cap 316. An operator should thoroughly wash and dry his or her hands prior to handling these synthetic calibration material standards and samples 310.

A cap 316 may be shaped and sized to engage and cover a window 14 or lens 14 of a barrel 13 of a photonic scanning device 10. In selected embodiments, a cap 316 may include an aperture 318 formed within a wall 320 or face 320. When inserted 314, the ball 313 may be positioned over the aperture 318 on the inside of the cap 316.

The shape and thickness of the face 320 into which the aperture 318 is formed may serve as a gauge for the ball 313 or glob 313 of test sample material 310. Typically, the ball 313 is on the order of between three and thirteen hundreds of a gram in mass. The face 320 may be sufficiently thin so the ball 313 of sample material 310 will extend inside the cap 316. Accordingly, a user may place a digit, such as a thumb or finger against the face 320 to covering the aperture 318 when placing the cap 316 over a lens 14 and barrel 13 of a photonic scanner system 10. The ball 313 may then deform between the user's digit, the edges of the aperture 318, and the window 14. Thus, a good complete contact is made against the window 14, without an individual touching the window 14, nor thinning out the ball 313 of material into a layer that is too thin to be properly opaque.

As a practical matter, a cap 316 in accordance with the present invention may have a rim 321 or collar 321 suitably formed to grip the barrel 13 associated with the window 14. An aperture 324 may be formed in an ear 322 extending from the collar 321. A lanyard 326 may connect to engage the aperture 324 in the ear 322. If desired, a lanyard 326 may include a loop 328 to preclude loss or to secure the cap 316 to the device 10.

In one embodiment of a calibration process, the dark cap may still be used. However, the two-sided calibration cap is replaced by a synthetic composition having a base composition of a silicone compound (also known and dilatant compound, the material commonly known as Silly Putty™). Various levels of dopants may be mixed with the base. Dopants may be naturally occurring compounds, but synthetics used in the film calibration system have been found to be suitable and stable if ground to powder and mixed into the base. There are several of these calibration standards. Each represents a different level of dopant including a neutral or undoped sample. This material may be distributed in tubes 302, each tube 302 containing enough material for a selected number of calibrations. This avoids "cap placement problems" in calibrating the scanner.

Once a ball 313 or glob 313 of sample material 310 has been properly positioned within a cap 316, an operator may apply 330 the cap 316 flush to the window 14 of the device 10. The sample material 310 may then be scanned 332 and the machine 10 calibrated accordingly. The sample material 310 may be discarded after a single use to prevent contamination. The machine 10 may be calibrated using a "white" scan, a low scan, and a high scan, as was done with the film cap system.

Following a scan 332 or series of scans 332, an output 334 may be provided produced by the photonic scanning apparatus 10 with its associated computational system. Typically, multiple scans 332 are run on multiple samples 310. As a practical matter, a blank or "white" material 90 having pigment but no doping provides a neutral sample. This material contains the dilatant compound with the standard pigmentation. Thus, the sample material 90 provides a white scan similar to the fluorescence of skin but with a total absence of the carotenoid effect on Raman scattering.

The low sample 92 may provide a sample size in the range including a typical lower limit on the Raman scattering effect in human skin. Similarly, a high sample or high-valued sample 94 may include a composition providing a scanned reading or value approximating that typically occurring at the upper limit of typical human skin response to Raman scattering. Similarly, one or more middle range samples 93 may provide intermediate value of scanning results, corresponding to a typical mid-range Raman scattering output expected from a scanning system 10.

Once sufficient data has been collected from the outputs 334 from scanning the multiple samples 90-94 multiple times, a decision 336 may be made. That is, if sufficient data has been collected, calibration 340 for the system 10 may be completed. Accordingly, the system 10 may be calibrated 340 according to the curve fitting, background elimination, normalization, and so forth. Nevertheless, until sufficient data is collected, a continued selection 338 of a next sample 310 from the materials 90, 92, 93, 94 available will continue iteratively. This selection 338 may continue iteratively on a single material 90, 92, 93, 94, as well as an iteration from material to material 90-94.

Figure 8:
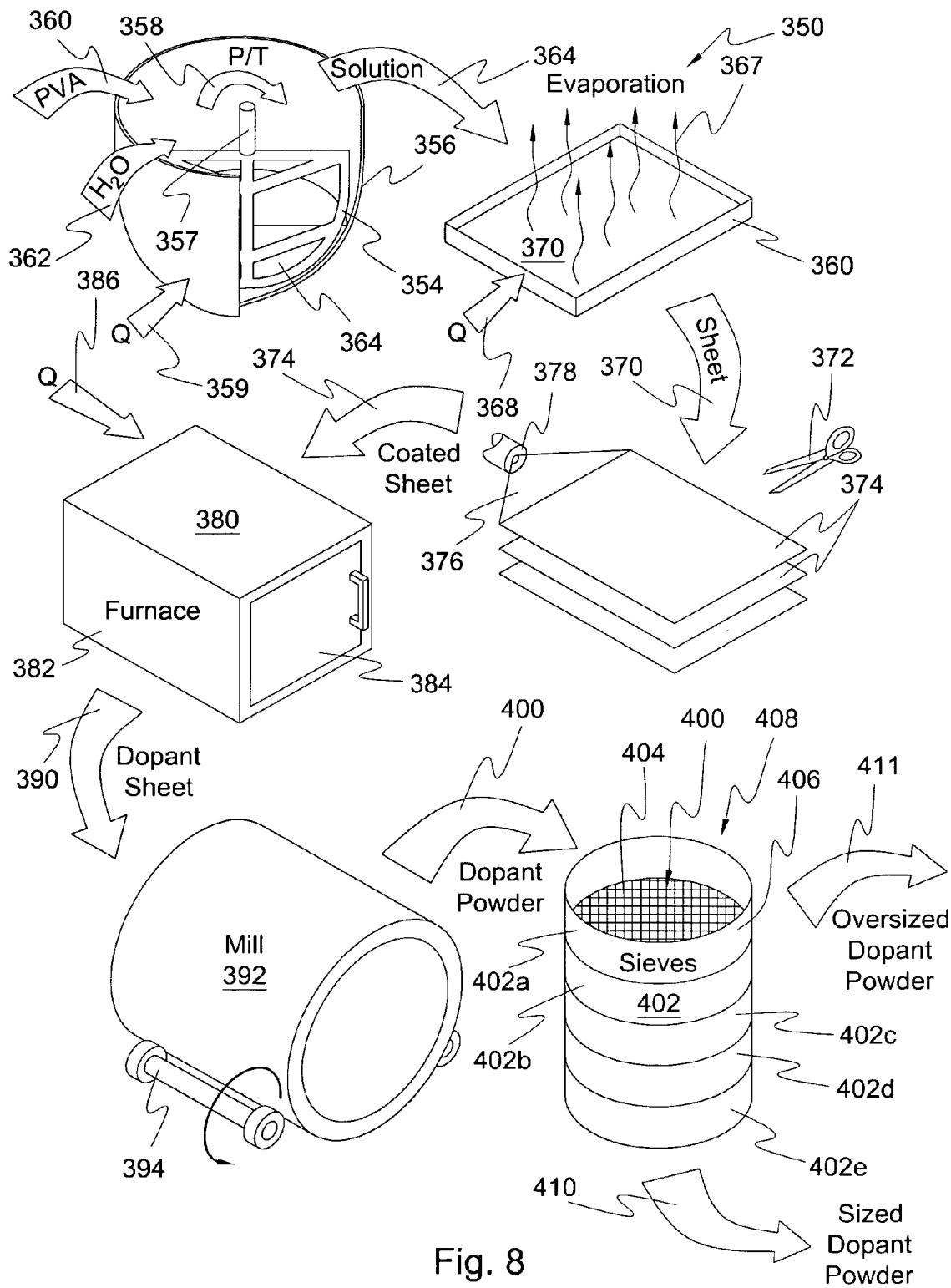
FIG. 8 is a schematic block diagram of a process for making a dopant in accordance with the invention.

Referring to FIG. 8, the dopant materials may be formed independently from conventional processes previously relied upon. For example, in one embodiment, a process 350 for forming a dopant material may include dissolving 352 with a mixer 354 driven by a shaft 357 in a container 356. Power 358 or torque 358 to the shaft 357 may enhance the speed of dissolving polyvinyl alcohol (PVA) 360 in water 362. The addition of heat 359 to maintain about one hundred eighty degrees Fahrenheit within about fifteen to twenty degrees may also enhance the speed of dissolving PVA 360 in water 362. Additionally, crystal size may vary, but smaller crystal sizes for the PVA 360 enhance the speed of dissolving 352. An "eighty percent" PVA 360, granulated, of molecular weight of about 9,000 to 10,000, has proven effective.

Ultimately, the mixer 354, which may be any mixing device of any suitable type, will eventually provide a solution 364. In one embodiment, the PVA 360 may be from about ten percent to about fifty percent of the solution, and water 362 may be the remainder. A ratio of about eighty-five percent water to about fifteen percent PVA 360 has shown to be consistently effective and adequately fast.

The solution 364 may be passed to a tray 366 where evaporation 367 may occur, typically enhanced by the addition of heat 368. Drying over a period of hours with heat 368, or a period of days without heat, much of the water 362 evaporates 367 leaving a somewhat rigid sheet 370. Typically, the solution 364 may be poured out onto the tray 366 for a depth of from about one half centimeter to about one and one half centimeters. Typically, a depth of from about one quarter centimeter to about one centimeter has been shown effective. Accordingly, after evaporation 367, the sheet 370 may have a thickness of about one to two millimeters.

While still warm, or after warming, the sheet 370 may be cut by a shear 372 or cutter 372 of some other type to provide a particular size that may be handled by subsequent machinery or individuals. Each sheet 370 may be coated to form a coated sheet 374. In selected embodiments, the coating applied may be a spray or other application of hydrochloric acid (HCL) 376 to one or more sides of the sheet 370. A nozzle 378 or other tool 378, such as an applicator 378 available it the chemical arts may serve to apply the HCL 376. Application of reagent grade HCL 376 solution of about thirty-six to thirty-eight percent commercially available has been found effective across the surfaces of sheets 370 on the order of one to three millimeters in thickness. Any commercial HCL 376 should work.

The coated sheets 374 may then be placed in a furnace 380 substantially closed in by walls 382 and a door 384 or other access 384 in order to effectively apply heat 386 to the coated sheets 374. The heat 386 may typically be applied for about an hour to a few hours, typically no more than three or four. It has been found that approximately one hour of heat with a maintained temperature of approximately 160 C is effective to react the coded sheet 374 to make a dopant sheet 390. A range of plus or minus forty degrees Celsius will work but one hundred twenty slows reaction rates, while over two hundred degrees Celsius begins to carbonize the sheet 390. Typically, a dopant sheet 390 may be in large monolith, but may be in chunks, or granules. The dopant sheet 390 leaves the original clear appearance of the sheet 370 and the coated sheet 374 to become a deep and dark orange color. The orange color reflects the chemical condition of the dopant sheet 390.

A mill 392 driven by some set of drivers 394 and appropriate power 396 may then be used to grind the dopant sheet 390. The mill 392 may be one of any suitable type known in the chemical processing arts. For example, a cryogenic mill, a hammer mill, a grinder, rotary mill 392, or the like may all operate suitably. In one embodiment, a ball mill 392 has been found effective, using either spheres, cylinders, or the like. Similarly, the media used to operate in such a mill 392 has been suitably shaped as cylinders of various sizes, spheres of various sizes, and a mixture of both.

From the mill 392, following operation for a period of hours or days, a dopant powder 400 or dopant 400 in a powdered form results. A cryogenic grinder will provide results immediately. A ball mill may take from one day to five days. Typically, by selective choice of media, one day to two days of operation of a ball mill has been found effective to provide a comparatively high percentage of suitable dopant 400. That is, the size of the mean diameter typically becomes smaller for the particulates in the dopant 400 with more time in milling. Yields on the order of thirty percent to about seventy percent mass of particles of number three hundred twenty-five sieve size have resulted. Typically with at least some steel balls as media in a mill 392, yields of approximately sixty percent have been found consistently. Milling time may vary from about one to four days and is typically two days, if steel spheres are used, to get a sixty percent yield of number three hundred twenty-five sieved particles.

Following grinding or milling of the dopant 390 to form the dopant powder 400, sieves 402 may sort the dopant 400 by size (mean size of particles). A series of sieves 402 may be used, where each sieve 402a-402e includes a screen 404 having a particular clearance size or mesh size. Typically, with dopant powders 400 made as described hereinabove, a screen mesh size over three hundred has been found effective. Moreover, a screen mesh size of three hundred twenty-five is used regularly. Using a mesh size corresponding to any number high than three hundred has not been shown to provide any improvement in results. Nevertheless, mesh sizes on the order of a number two hundred have been used successfully. A number two hundred seventy sieve and larger sizes do show more variation in the quality of Raman scattering from the dopant 400.

Each of the sieves 402 is formed of a wall 406 or rim 406 maintaining the screen 404 therein as a substantially planar material. The sieves 402 may be stacked in a stack 408 and placed in a vibration device as known in the art in order to enhance the speed at which the dopant 400 passes through each of the screens 404.

Ultimately, a sized dopant particulate 410 may result from the smallest sieve 402e used. Typically, a sieve having a number 300 has been found consistently suitable, with no substantial improvement noticeable by any smaller sizes. Nevertheless, in some commercial materials, a sieve mesh size as large as 200 has been found suitable. Nevertheless, the 200 mesh has been most suitable with materials that include the dopant material on a substrate, and thus may result in a suitable particle, of a larger size, whereas the dopant 400 is used in a more pure form, and thus may be comminuted to a smaller size to obtain the same concentration. Oversized dopant 411 may be recycled through the mill 392. In practice, no degradation has been observed in the oversized dopant powder 411 or particulates 411 by continued milling in the mill 392.

Figure 9:
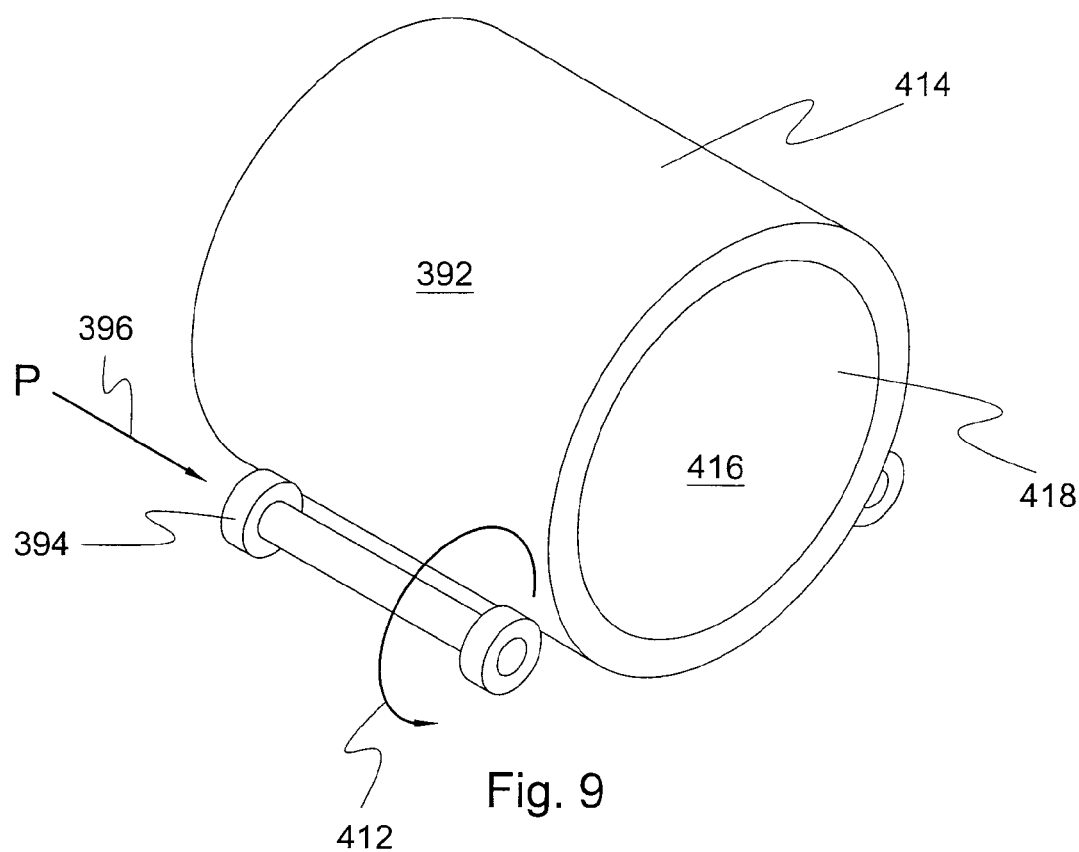
FIG. 9 is a schematic diagram of a mill for grinding a dopant in accordance with the invention.
Figure 10:
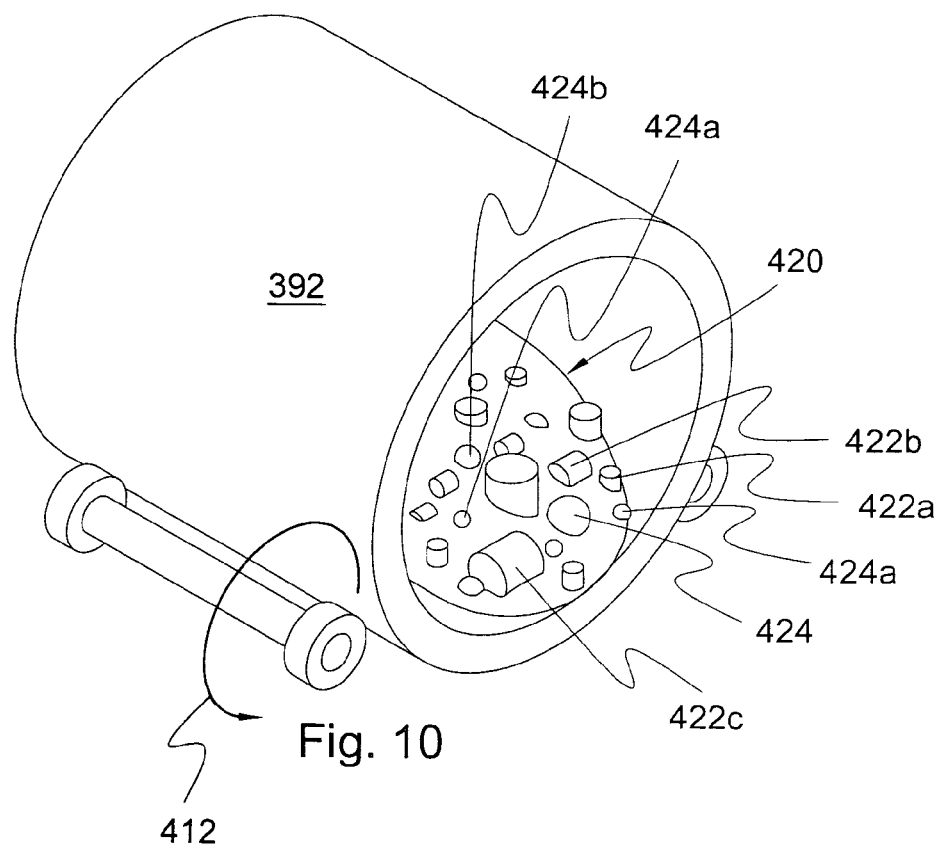
FIG. 10 is a schematic diagram of a process and apparatus for grinding a dopant in accordance with the invention.

Referring to FIGS. 9-10, in one embodiment of a ball mill 392, a torque 412 may be applied to a driver 394 or set of rollers 394 driving a drum 414 or container 414. The drum 414 may have an access 416, such as a door 416 or other closure 416. Upon opening the door 416, an opening 418 may provide for feeding and removal of material and media. Typically, the media 420 may include various sizes and shapes of heavy and hardened materials. That is, ceramic cylinders, ceramic balls, steel balls, steel cylinders, and the like may serve a media 420.

Cylinders 422 have been found effective in multiple sizes, such as approximately one centimeter diameter by approximately one centimeter or to one and a half centimeters in length, as well as an intermediate size of approximately double those dimensions, and a larger size of approximately triple the dimensions of the smallest units. For example, diameters on the order of one centimeter, two centimeters, and three centimeters seem to serve, while lengths from approximately equal thereto up to about fifty percent greater have been found suitable. Similarly, steel balls of those dimensions appear to serve adequately. A mixture thereof also works well. Ceramic or steel cylinders, spheres, or a mixture thereof may serve well.

Figure 11:
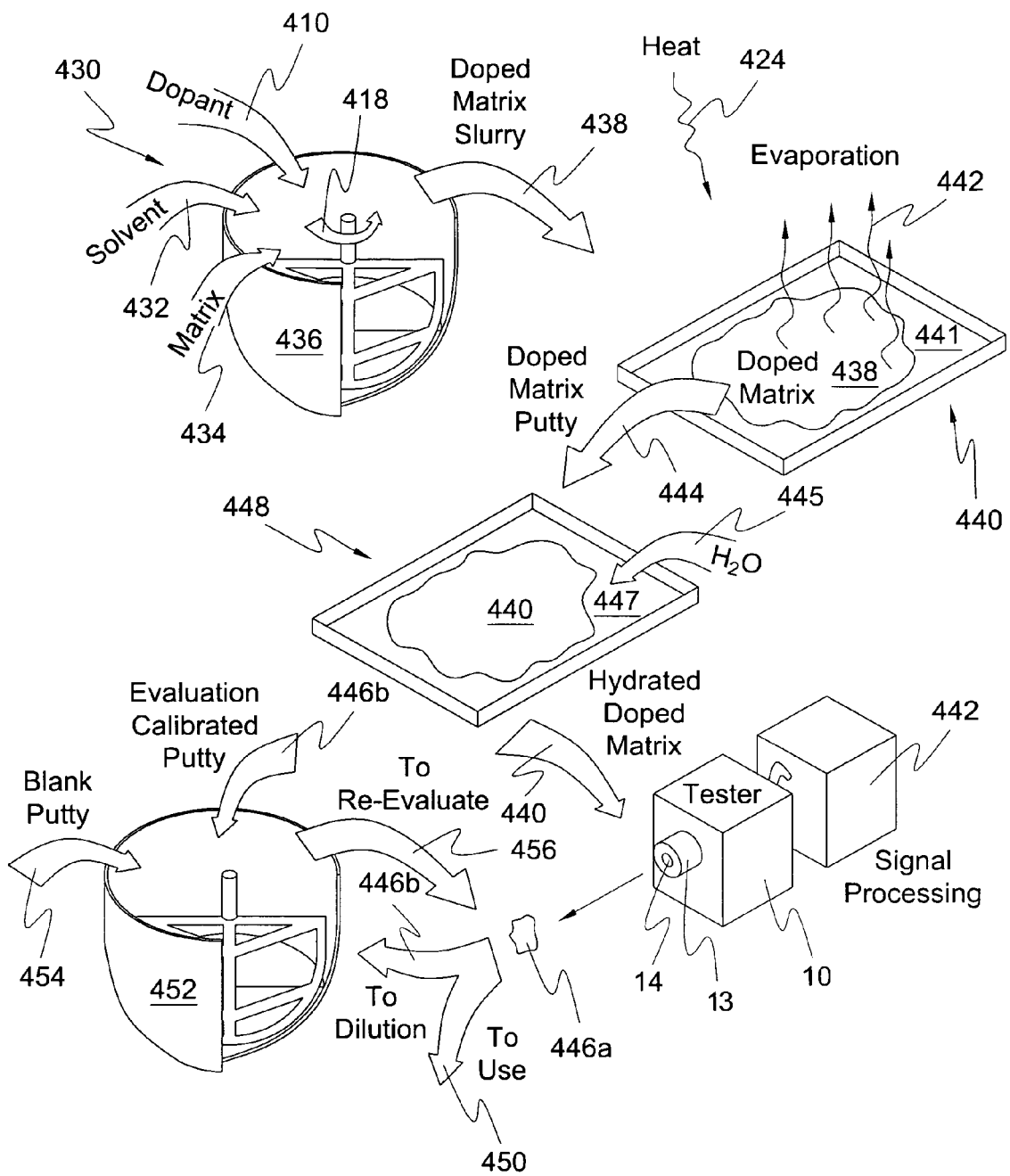
FIG. 11 is a schematic block diagram of a process for compounding a calibration composition in accordance with the invention.

Referring to FIG. 11, a process 430 suitable for formulating the master samples 30, such as the low valued sample 92, medium valued sample 93, and high valued sample 94 may begin by adding a solvent 432 to a matrix 434 of dilatant compound 434. The matrix 434 may benefit from approximately an equal mass or volume of a solvent 432 such as ethanol. Sufficient solvent 432 may be added to the matrix 434 in a mixer 436 to provide a slurry 438 easily poured. Thus, a consistency similar to that of cake batter or other slurries has been found suitable. Since the solvent 432 will eventually be evaporated, the amount of solvent 432 does not need to be controlling, so much as the ability to handle the slurry 438. Blending may be done in a matter of minutes, typically about ten minutes, depending on equipment and batch size.

The matrix 434 in one embodiment has been mixed with a dopant 410 in order to provide a completely doped slurry 438. In certain embodiments, the dopant 410 may be added without the solvent 432. Nevertheless, clumping of the dopant particles 410 has been observed. Observable static electricity, particularly in the presence of the matrix 434, leads Applicants to believe that the dielectric nature of both the dopant 410 and the matrix 434 may be assuaged or ameliorated by the addition of solvent 432. The solvent 432 may act as an electrical conductor or may simply act as a material to exert surface tension over the particulate dopant 410, while also rendering the slurry 438 more easily handled.

The slurry 438 may be delivered into a chamber 440 containing a tray 441. That is, a chamber 440 suitable for drawing off or conducting off the solvent 432 in an evaporation process 442 results in a suitable putty 444. If desired, the doped putty 444 may have added to it a certain amount of water 445 in order to form a hydrated putty 446. Typically, a mere ten milliliters to about thirty milliliters per kilogram of the doped putty 444 has been found effective to form a more easily handled and shaped hydrated putty 446. Typically, ten milliliters of water in half a kilogram of the doped putty 444 has been found to provide a suitable hydrated putty 446 upon proper kneading 448 in some suitable container 447, mixer 447, or the like. Kneading 448 may be done by a machine, or by hand, depending on the quantities desired.

The hydrated putty 446, constituting a doped matrix of dilatant compound may be scanned in small samples 446a by irradiation through a lens 14 of a barrel 13. Processing by a suitable computer system described hereinabove may provide an evaluation. Thus, a determination may be made as to whether the sample 446a is suitable to use 450. That is, sample 446a may have the proper doping to become one of the master samples 30 (90, 92, 93, 94).

Nevertheless, it has been found that above approximately sixty grams of dopant 410 per kilogram of matrix 434, the Raman scattering is excessively bright. Accordingly, if the Raman scattering from the proper irradiance by the apparatus 10 is higher than desired, then the material 446a may be sent as dilution material 446b. That is, the batch of hydrated, doped-matrix putty 446 may be sent to a mixer 452. The mixer 452 may be of any suitable type, from manual kneading to commercial, powered mixers 452. In the mixer 452 or an associated process, blank putty 454 corresponding to the matrix 434, or a hydrated amount of the matrix material 434 may be added to the evaluated putty 446b to form a new diluted putty 456 later re-submitted for reevaluation 456.

Applicants have found that once a particular concentration of dopant 410 has been properly kneaded into or mixed into a hydrated putty 446, it can be "cut" (diluted) by any suitable amount of blank putty 454 containing no dopant, in order to obtain a precise percentage of dopant 410. Accordingly, the response from each sample 446a can be engineered to obtain a comparatively precise Raman response.

Figure 12:
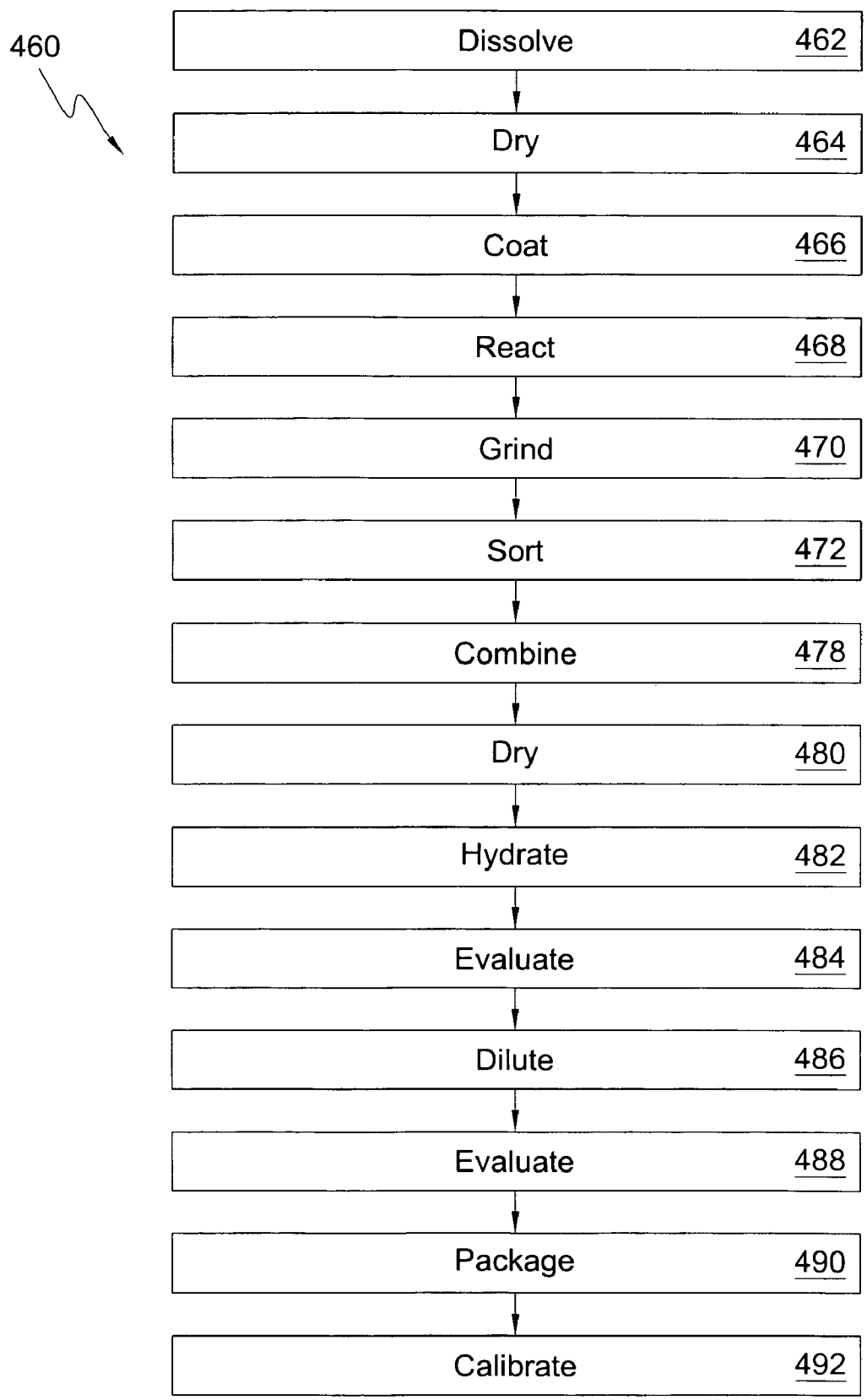
FIG. 12 is a schematic block diagram of a process for making and using a synthetic calibration composition in accordance with the invention.

Referring to FIG. 12, a process 460 for preparation of a suitable putty for use 450 may involve dissolving 462 polyvinyl alcohol with water in a ratio of about one part alcohol to five parts water. This may be done by weight or volume, since the specific gravity of polyvinyl alcohol is only slightly above that of water.

Next, the solution resulting from dissolving 462 may be dried 464 by the application of ventilation, air, heat, or a combination thereof in order to provide a film on the order to one to three millimeters in thickness, in certain embodiments. Coating 466 these layers of sheet PVA 370 with hydrochloric acid provides the materials for a suitable reaction 468. The hydrochloric acid has been found to be a standard reagent grade. One typical embodiment involves from about thirty-five percent to about forty percent hydrochloric acid solution at a reagent quality. The reaction 468 may be enhanced by the addition of heat, and maintenance at a temperature of about 160 C. A variation in temperature of about forty degrees higher or lower may degrade the quality of the reaction. Thus, below 120 C tends to promote less vigorous reaction, whereas temperatures above 200 C appear to tend to degrade and carbonize the resulting material.

After the reaction 468, the resulting dopant sheets 390 may be ground 470 by any suitable process. Many suitable mills exist, and Applicants have found a ball mill to be adequate, although not particularly fast. Cryogenic grinding systems are used in the chemical processing industry, and may also perform the grinding function.

Following grinding 470, sorting 472 by a system of sieves 402 provides a sized dopant powder 410, as well as an oversized dopant powder 411. Oversized powder may be recycled through the mill 392, while the properly sized dopant powder 410 may be taken for use.

The process 460 may continue with a combination 478 or combining 478 the dopant 410 along with a matrix 438 of dilatant compound or other matrix 434 and a suitable solvent 432. Following a complete mixing 478, the mixture may be dried 480 by application of modest temperatures, and ventilation.

The resulting doped putty 444 may be hydrated 482 for easier handling and packaging. In order to establish a particular and specific amount of dopant 410 per gram or kilogram of the hydrated putty 446, a dilution 486 with blank putty 454 may introduce a proper amount of undoped putty 454. Following a repeat of the evaluation 484 and dilution 486 until an evaluation 488 results in a product suitable for use 450, results in a system 30 or master set 30 of samples ranging from a neutral 90 to a low 92, one or more medium-valued samples 93, and a maximum or high-valued sample 94. Packaging 490 may include placement of the suitably hydrated matrix material 456 ultimately resulting into a system of tubes 302 for easy extrusion and use of small samples 310 on the order of 0.1 to 0.01 grams each. Typically, a quantity from about 0.03 to about 0.1 grams has been found suitable, as has any larger amount. Thereafter, calibration may occur using the master samples 30.

The present invention may be embodied in other specific forms without departing from its essential characteristics. The described embodiments are to be considered in all respects only as illustrative, and not restrictive. The scope of the invention is, therefore, indicated by the appended claims, rather than by the foregoing description. All changes within the meaning and range of equivalency of the claims are to be embraced within their scope.

What is claimed and desired to be secured by United States Letters Patent is:

1. A method of making a synthetic dopant to provide Raman scattering corresponding to a compound of interest detectable non-invasively, non-destructively, in-vivo by a scanner, the method comprising:
   determining a characteristic bond existing in the compound and detectable by the scanner;
   providing a base material;
   providing a reactant effective to react with the base material to form a dopant containing the characteristic bond;
   providing a carrier; and
   distributing the dopant in the carrier at a concentration effective to mimic the response of the compound of interest when scanned by the scanner.

2. The method of claim 1, wherein the base material is a hydrocarbon.

3. The method of claim 2, wherein the reactant is an acid.

4. The method of claim 3, wherein the dopant is a solid.

5. The method of claim 4, further comprising comminuting the dopant to a size effective to provide uniformity of response to illumination by the scanner over substantially an entire batch of the carrier mixed with the dopant.

6. The method of claim 5, wherein the base material is polyvinyl alcohol.

7. The method of claim 6, wherein providing the base material further comprises dissolving the base material in a solvent.

8. The method of claim 7, further comprising comminuting the dopant to a size to fit through a sieve sized from about a number 200 sieve to about a number 400 sieve.

9. The method of claim 8, wherein the reactant is hydrochloric acid, the characteristic bond is a carbon-to-carbon double bond, and the method further comprises heating the base material and hydrochloric acid to from about 140 degrees Fahrenheit to about 200 degrees Fahrenheit to accelerate the reaction therebetween.

10. The method of claim 9, wherein the scanner illuminates with laser light and detects Raman scattering of an illuminated subject.

11. A method of calibrating a scanner illuminating tissue in vivo, non-destructively, and non-invasively to detect a Raman scattering response thereto, the method comprising:
   forming a matrix material pigmented to provide a fluorescence response corresponding to that of tissue in response to the scanner;
   forming a dopant providing a Raman scattering response corresponding to that of tissue;
   mixing the matrix material and dopant to form a standard;
   evaluating the standard for a Raman scattering response thereof;
   diluting the standard with additional matrix material; and
   ceasing dilution at a pre-determined value of Raman scattering response of the standard.

* * * * *